United States Patent [19]

Klosowski et al.

[11] 4,104,295
[45] Aug. 1, 1978

[54] METHYLSILACYCLOPENTENYL-CONTAINING SILYLATING AGENTS AND METHOD THEREFOR

[75] Inventors: Jerome M. Klosowski, Monitor Township, Bay County; Charles A. Romig, Midland, both of Mich.

[73] Assignee: Dow Corning Corporation, Midland, Mich.

[21] Appl. No.: 737,744

[22] Filed: Nov. 1, 1976

[51] Int. Cl.² ............................................. C07F 7/10
[52] U.S. Cl. ..................... 260/448.2 N; 260/448.2 D; 260/448.2 E
[58] Field of Search ................. 260/448.2 N, 448.2 D, 260/448.2 E

[56] References Cited

U.S. PATENT DOCUMENTS 3,509,191   4/1970   Atwell .......................... 260/448.2 D Primary Examiner—Paul F. Shaver
Attorney, Agent, or Firm—George A. Grindahl

[57] ABSTRACT

Methylsilacyclopentenyl-containing amides and lactams, such as methylsilacyclopentenyl-N-methylacetamide and methylsilacyclopentenyl-epsilon-caprolactam are disclosed. These compounds display unexpected silylating ability when mixed with an active-hydrogen-containing compound. In particular, organic and organosilicon compounds having at least one —OH, —SH,

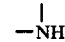

or —NH₂ group are readily converted to a methylsilacyclopentenyl derivative.

6 Claims, No Drawings

METHYLSILACYCLOPENTENYL-CONTAINING SILYLATING AGENTS AND METHOD THEREFOR

BACKGROUND OF THE INVENTION

This invention relates to silylation of an active-hydrogen-containing compound. In one aspect this invention relates to new methylsilacyclopentenyl-containing compounds which possess unexpected silylating power.

Silylation of active-hydrogen-containing organic compounds for the purposes of chromatographic analysis, organic synthesis and blocking and/or protecting reactive sites in the organic molecule is a well-known and useful procedure. A large number of trimethylsilyl-containing silylating agents and silylating procedures are reviewed by Alan E. Pierce, "Silylation of Organic Compounds," Pierce Chemical Company, Rockford, Illinois (1968).

Silylating agents which provide the trimethylsilyl group are usually used for such purposes because of their commercial availability and because of the desired properties of the resulting trimethylsilylated organic compound, such as higher volatility compared to the unsilylated compound. However, other factors, such as silylating power, and the nature of silylation byproducts often are also important in the selection of a silylating agent.

Of the known silylating agents, bis-trimethylsilylacetamide (hereinafter BSA), provides both availability and high silylating power. However, BSA contains two trimethylsilyl groups, the first of which is responsible for BSA's silylating power. The second trimethylsilyl group in BSA, which remains after the first trimethylsilyl group is reacted is less reactive than the first trimethylsilyl group. Consequently, it is common to use one mol of BSA for each active hydrogen atom to be silylated in a silylation reaction and the by-product, trimethylsilylacetamide, is not used in the reaction. Thus, only one-half of the available trimethylsilyl groups are used. A more efficient silylating agent having high silylating power is desired.

We have discovered that silylating agents bearing a methylsilacyclopentenyl group which is bonded to an amido radical or a lactamo radical are powerful and efficient silylating agents.

Methylsilacyclopentenyl-containing compounds bearing a silicon-bonded halogen atom or a silicon-bonded alkoxy radical are disclosed by Atwell in U.S. Pat. No. 3,509,191 which is hereby incorporated by reference to show the preparation of methylsilacyclopentenyl chloride which is a precursor for the preparation of methylsilacyclopentenyl amides and lactams.

Hahn, in U.S. Application No. 644,379, titled "Silacyclopentenyl-bis-epsilon-caprolactam," filed on December 29, 1975 and assigned to the assignee of this invention discloses the title compound and its use as a chain extender for hydroxyl compounds, and especially hydroxyl-endblocked polydimethylsiloxanes, for which it is a very fast chain extender. However, chain extension is a polymerizing process which greatly increases molecular weight and decreases volatility of the polydimethylsiloxane. Such a result is not suitable in a silylating process.

Toporcer, et al., U.S. Pat. No. 3,776,933 discloses a method of preparing amidosilanes of the formula $R_x''Si\{N(R)C(=O)R'\}_{4-x}$ wherein $R''$ is a monovalent hydrocarbon radical having 1 to 18 carbon atoms and $x$ = 1 to 3. Toporcer, et al., state that said amidosilanes are useful as crosslinking agents in silicone rubber, as hydrolyzable silanes to make silicone resins, as chain extenders in silicone rubbers, as endblockers in silicone fluids, as silylating agents and the like. However, Toporcer, et al., do not suggest that methylsilacyclopentenyl amides could be made or that they would be superior silylating agents. U.S. Pat. No. 3,776,933 is hereby incorporated by reference to show a suitable method for preparing the siliconamide bond.

Silicon-bonded lactams are known from Hurwitz and de Benneville in U.S. Pat. No. 2,876,209 and U.S. Pat. No. 2,876,234. Hurwitz and de Benneville describe silanes containing the lactam group where the generic formula is

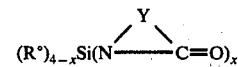

in which $R°$ is a cyclohexyl group, an aryl group, an alkenyl group or an alkyl group having 1 to 18 carbon atoms, Y is an alkylene group having 3 to 18 carbon atoms with a chain of at least 3 but no more than 5 carbon atoms extending between the N atom and carbonyl group, and $x$ is an integer having a value of 1 to 4. U.S. Pat. No. 2,876,234 is hereby incorporated by reference to show the preparation of the lactam silicon bond.

SUMMARY OF THE INVENTION

It is an object of this invention to provide new silylating agents.

It is another object of this invention to provide new methylsilacyclopentenyl compounds.

It is another object of this invention to provide a powerful and efficient silylating agent.

It is a further object of this invention to provide a new method for rapidly and efficiently silylating active-hydrogen-containing compounds.

These and other objects, which will be apparent on consideration of the following specification and appended claims, are obtained by mixing a methylsilacyclopentenyl amide or lactam of this invention with a compound bearing at least one hydrogen atom which is bonded to an oxygen, nitrogen or sulfur atom. The active hydrogen is replaced with a methylsilacyclopentenyl group at a rate which is unexpectedly faster than the rate of the reaction of the corresponding amide or lactam bearing a triorganosilyl radical.

DESCRIPTION OF THE INVENTION

This invention relates to a composition having the formula

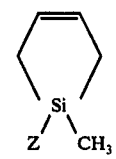

(I)

wherein Z is a monovalent organic radical selected from the group consisting of amido and lactamo.

This invention further relates to a method of silylating an active-hydrogen-containing compound which comprises mixing a composition of this invention having the formula (I) with said active-hydrogen-containing compound.

The composition of this invention consist of a methylsilacyclopentenyl radical bonded to either an amido radical or a lactamo radical.

By a methylsilacyclopentenyl radical it is meant a radical having either of the following isomeric formulae wherein the unfilled silicon valence is bonded to another radical such as amido.

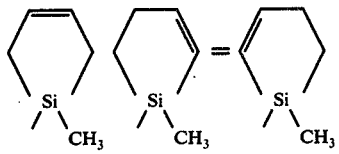

In a method for the preparation of methylsilacyclopentenyl chloride, as disclosed by U.S. Pat. No. 3,509,191 hereinabove incorporated by reference, 1,4-butadiene is heated with $(CH_3)_3Si_2Cl_3$ at 550° C. to produce a mixture of isomeric chlorosilanes having the formulae

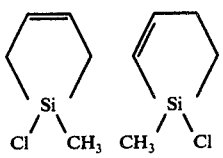

These isomers are, individually or in mixture, are preferred intermediates for the preparation of the compositions of this invention. The formula (I) is accordingly intended to include both

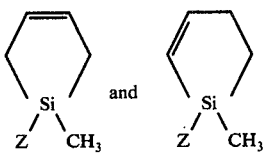

and their mixtures.

By amido radical and lactamo radical it is meant the monovalent organic radical that is obtained when a nitrogen-bonded hydrogen is removed from an organic amide or a lactam, respectively.

The amido radical has the general tautomeric structure.

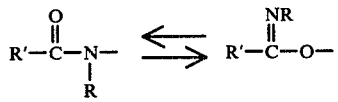

For the purposes of this invention R and R' are selected from the group consisting of hydrogen and monovalent hydrocarbon radicals having from 1 to 8 inclusive carbon atoms. Suitable amido radicals include formamido, acetamido, N-methylformamido, N-methylacetamido, N-ethylacetamido, N-t-butylacetamido, N-vinylacetamido, N-tolylacetamido, N-phenylacetamido, propionamido, N-methylpropionamido, benzamido and N-methylbenzamido.

The lactamo radical has the general tautomeric structure

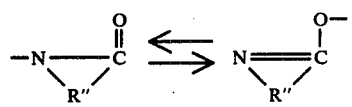

For the purpose of this invention R" is a divalent alkylene radical having from 3 to 8 carbon atoms such as $-(CH_2)_3-$, $-(CH_2)_4-$, $-(CH_2)_5-$, $-CH_2CH_2CH(CH_3)CH_2CH_2-$, and $-(CH_2)_8-$.

The compositions of this invention may be prepared by any suitable method. In a preferred method for preparing silylamides and silylactams, methylsilacyclopentenyl chloride is mixed with an appropriate amide or lactam, bearing at least one hydrogen bonded to nitrogen, in the presence of an anhydrous solvent and at least a sufficient amount of a suitable HCl acceptor such as a tertiary amine such as triethylamine to react with any HCl by-product. Another method for preparing silylamides, which is suitable for the preparation of methylsilacyclopentenyl amides of this invention, is disclosed by Toporcer, et al. in U.S. Pat. No. 3,776,933 hereinabove incorporated into this disclosure by reference. Another method for preparing silyl lactams, which is suitable for the preparation of methylsilacyclopentenyl lactams of this invention is disclosed by Hurwitz, et al. in U.S. Pat. No. 2,876,234, hereinabove incorporated into this disclosure by reference.

It is to be understood that the formulae and the names that are used herein to denote the compositions of this invention are to be construed in such a manner as to encompass those methylsilacyclopentenyl amides and methylsilacyclopentenyl lactams which bear, as the case may be, a silicon-nitrogen bond or a silicon-oxygen bond or an intermediate form of bonding represented by a tautomeric equilibrium between Si-N bonding and Si-O bonding or any other form of bonding which may be regarded by those skilled in the chemical arts as being consistent with the chemical and physical behavior of the compositions of this invention. The reader is referred to chapter 4 of the textbook by Pierce, cited above, for a discussion of the Si-O and Si-N bonding in silyl amides and the various factors which may determine the type of bonding in any particular silyl amide.

For example, methylsilacyclopentenyl-N-methylacetamide, a preferred composition of this invention is understood to mean any one or more of the following structures or their equivalents consisting of a methylsilacyclopentenyl radical bonded to an N-methylacetamido radical.

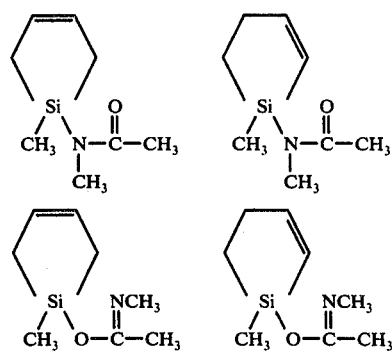

In like manner, methylsilacyclopentenyl-epsilon-caprolactam, another preferred composition of this invention, is understood to mean any one or more of the following structures or their equivalents consisting of a methylsilacyclopentenyl radical bonded to an epsilon-caprolactamo radical.

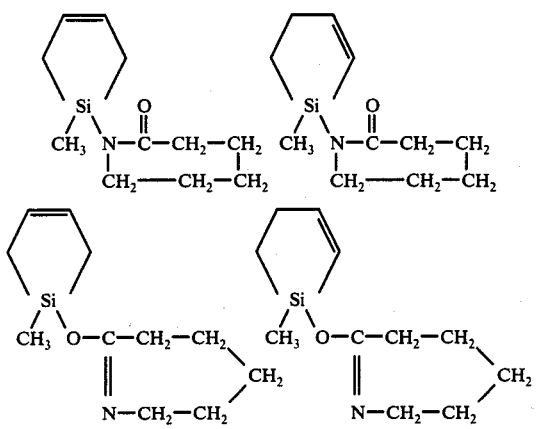

The compositions of this invention have unexpected silylating power. By the terms silylating and silylation it is meant a process wherein an active-hydrogen, i.e. one bond to an oxygen, sulfur or nitrogen atom, in a compound is replaced with a hydrocarbon-substituted silyl radical. Silylation, according to the process of this invention proceeds rapidly and, in many cases, essentially quantitatively thereby replacing an active-hydrogen with a methylsilacyclopentenyl radical. By silylating power it is meant the ability of a silylating agent to silylate isopropyl alcohol as indicated by the half-life of the silylating agent in excess isopropyl alcohol at 35° C., using standard chemical kinetic measuring methods hereinafter described. Silylating power is inversely related to said half-life.

The compositions of this invention are useful in the method of this invention for silylating an active-hydrogen-containing compound which comprises mixing a compound comprising at least one active hydrogen atom directly bonded to a heteroatom selected from the group consisting of oxygen, sulfur, and nitrogen and a silylating agent having the formula

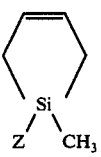 (I)

wherein Z is a monovalent organic radical selected from the group consisting of amido and lactamo, whereby a compound comprising at least one radical of the formula

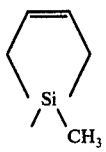

directly bonded to said heteroatom is obtained.

Active-hydrogen-containing compounds which may be silylated according to the process of this invention include any chemical compound having the general formulae QOH, QSH, $Q_2NH$, and $QNH_2$ wherein Q represents a monovalent radical which may or may not contain additional active hydrogen and may be any chemical moiety such as a hydrogen atom, a carbon-containing radical, a silicon-containing radical, and a carbon-free radical.

In the case where Q is hydrogen, silylation of the compound with (I) may proceed once per molecule to give rise to the corresponding methylsilacyclopentenyl hydroxide, mercaptan or amine, i.e. the corresponding silanol, silanethiol or silylamine or silylation may proceed more than once per molecule to varying degrees, to give rise to varying amounts of the corresponding disiloxane, disilthiane, disilazane or trisilylamine.

Carbon-free Q radicals include —OH, —$SONH_2$, —$NH_2$, —SH, which gives rise to inorganic compounds such as $H_2O_2$, $NH_2OH$, $HSO_2NH_2$, $NH_2NH_2$ and $NH_2SH$. Silylation of said inorganic compounds may or may not occur more than once per molecule in the process of this invention.

The method of this invention is of particular value for silylating compounds wherein Q is a carbon-containing radical, a silicon-containing radical or an organosilicon radical containing carbon and silicon atoms.

In particular, any organic compound bearing at least one hydrogen atom bonded to oxygen, sulfur or nitrogen may be silylated by the method of this invention. Illustrative of such organic compounds are alcohols, phenols, enols, hydroperoxides, peroxy acids, carboxylic acids, thiocarboxylic acids, mercaptans, sulphonic acids, sulfinic acid, sulfonamides, sulfate esters, phosphate esters, phosphonic acids, phosphonous acids, phosphinous acids, amines, hydroxylamines, aminoacids, amides, imides, amidines, ureas, oximes, carbohydrates, steroids, and alkaloids and other natural products. Said organic compound may or may not further comprise other groups such as one or more ester, nitrile, nitro, carbonyl, ether, sulfide, acetal, ketal, C=C, C|C, aromatic, aliphatic, cycloaliphatic, heterocyclic and halogen groups.

The method of this invention also encompasses chemical compounds wherein the Q radical contains silicon or silicon and carbon, giving rise, in either case, to a silicon-containing compound.

Silicon-containing compounds free of carbon, include but are not limited to, siliceous materials such as silica, sand, ground quartz and polysilicic acid wherein the active hydrogen is bonded to an oxygen atom which is bonded to a silicon atom.

Silicon-containing compounds containing both carbon and silicon atoms which may be silylated in the method of this invention include organosilicon compounds such as silanes such as silanols, silthiols and silylamines and polysilicon compounds such as siloxanes, silthianes and silazanes. Of particular interest are the hydroxy-containing polyorganosiloxanes such as fluids, gums and resins wherein the organic groups are monovalent hydrocarbon groups such as methyl, ethyl, vinyl, phenyl and 3,3,3-trifluoropropyl which are bonded to silicon by a silicon-carbon bond and the hydroxyl groups are directly bonded to a silicon atom by a silicon-oxygen bond.

It is to be understood that the compound to be silylated by the method of this invention may contain one or more active hydrogens and said active hydrogens may be bonded to the same type or different types of heteroatoms. Furthermore, the compound to be silylated may be a simple compound or a mixture of compounds, at least one of which bears at least one active hydrogen bonded directly to oxygen, sulfur or nitrogen.

It is to be understood that one or a mixture of more than one of the silylating agents of this invention may be used in the method of this invention.

The method of this invention is particularly useful for derivatizing organic compounds, such as natural products, which are high-boiling, thermally sensitive or reactive. Silylation has a stabilizing action so that subsequent operations such as distillation, gas chromatographic analysis and/or selected chemical reaction may be conducted on the silylated organic-compound. The method of this invention is additionally useful for silylating active-hydrogen-containing polymers, thereby endblocking the polymers, modifying the surface characteristics of natural polymeric fibers and introducing silacyclopentenyl unsaturation into an active-hydrogen-containing polymer.

In the method of this invention mixing may be done in any suitable fashion such as by blending, milling, stirring and shearing and in any suitable medium such as in solution or dispersion or in the absence of any solvent or dispersant. Preferably anhydrous conditions should be maintained during the silylating method of this invention.

Silylation takes place spontaneously upon mixing the reactants at any suitable temperature. In many cases rapid and essentially quantitative silylation will occur at room temperature within a few minutes. In some cases it may be desirable to conduct the silylation at an elevated temperature, for example, up to 100° C. or the reflux temperature of any solvent or dispersant, to achieve quantitative silylation in a convenient length of time. It is also within the scope of this invention to use any of the well-known catalysts and promoter solvents in the method of this invention.

The active-hydrogen-containing compound and the silylating agent may be mixed in any proportion. That is to say, the method of this invention is adaptable for either partial or complete silylation of an active-hydrogen-containing compound. In the simple case silylation comprises the reaction of one molecule of the silylating agent of this invention for every active hydrogen in the compound to be silylated. Thus, according to this stoichiometry, mixing of an equivalent amount of active-hydrogen-containing compound with silylating agent (I) will result in essentially complete silylation of said compound whereas mixing a more-than-equivalent amount of said compound will result in partial silylation of said compound. If desired, a less-than-equivalent amount of said compound may be used in the process of this invention; however, any mixture comprising an amount of (I) in excess of that required by the above stoichiometry will be wasteful of the silylating agent. An equivalent amount of the compound to be silylated is that amount of compound, as measured in mols that will provide one mol of active hydrogen atoms for every mol of (I).

Surprisingly, the silylating power of the compositions of this invention exceed the silylating power of their triorganosilyl analogs. For example, the silylating power of methylsilacyclopentenyl-N-methylacetamide is greater than that of trimethylsilyl-N-methylacetamide, dimethylvinylsilyl-N-methylacetamide, dimethylphenylsilyl-N-methylacetamide and dimethyl-3,3,3-trifluoropropylsilyl-N-methylacetamide.

This invention further provides new silylating agents which are more efficient and of comparable silylating power compared to the well-known silylating agent, BSA.

The following examples are provided for purposes of illustration and to show the best mode known by us at this time of carrying out this invention and are not to be construed as limiting the invention which is properly delineated by the appended claims.

EXAMPLE 1

Methylsilacyclopentenyl chloride, 1 mol, was added over a period of 30 minutes to an anhydrous solution of 750 ml. of toluene, 146 g. of triethylamine and 1.05 mol of epsilon-caprolactam in a flask. After 1 hour of stirring the reaction mixture was filtered to remove $(CH_3CH_2)_3N.HCl$ and the filtrate was fractionally distilled to give a moderate yield of methylsilacyclopentenyl-epsilon-caprolactam, b.p. = 120° to 140° C. at approximately 0.5 kilopascals of pressure. Infrared spectroscopy indicated that the bonding in this silyl lactam, between the methylsilacyclopentenyl radical and the epsilon-caprolactamo radical, is predominently silicon-nitrogen bonding.

EXAMPLE 2

Methylsilacyclopentenyl chloride, 5 mols, was added to a slurry of 5.5 mols of the sodium salt of N-methylacetamide in 1500 ml. of dry toluene in a flask at such a rate as to keep the reaction mixture at a temperature below 60° C. After the addition of the chloride had been completed, the reaction mixture was stirred for 2 hours at room temperature, filtered to remove NaCl and the filtrate was fractionally distilled to give a moderate yield of methylsilacyclopentenyl-N-methylacetamide, b.p. = 76° to 87° C. at approximately 0.1 kilopascals of pressure. Infra-red spectroscopy indicated that the bonding in this silylamide, between the methylsilacyclopentenyl radical and the N-methylacetamido radical, is predominently silicon-nitrogen bonding.

EXAMPLE 3

Standard nuclear magnetic resonance (n.m.r.) tubes, 5 mm. O.D. × 205 mm. long, were first charged with 0.1 ml. of the silylating agents listed in the Table and then with 0.5 ml. of anhydrous isopropyl alcohol using a dry box to insure anhydrous conditions. Immediately after the addition of isopropyl alcohol the tubes were stoppered, inverted at least once to mix the reactants, removed from the dry box, and, within 30 seconds after the addition of isopropyl alcohol, were placed in a varian A-60 $^1H$ n.m.r. spectometer at 35° C. The n.m.r. spectrometer was preset to record the signal of the hydrogen atoms in the silicon-bonded methyl group. In repeat experiments the n.m.r. spectrometer was preset to record the signal of the hydrogen atoms in the methyl groups of N-methylacetamide or the nitrogen-bound hydrogen atom in epsilon-caprolactam. Where possible the reaction was followed by taking several readings of the appropriate n.m.r. signal intensity over a period of time. A plot of these data vs. time provides the time required for the concentration of any particular silylating agent to be reduced to ½ of its original concentration; a time known as the half-life of the silylating agent.

The compositions of this invention have a half-life which is too short to measure by this technique since they are completely reacted before the reaction mixture is placed in the n.m.r. spectrometer.

TABLE

| Silylating Agent | Half-life in Excess Isopropanol (min.) |
| --- | --- |
| $CH_2=CHSi(CH_3)_2$<br>$\quad\quad\quad\;\;\|$<br>$\quad\quad\quad CH_3NCOCH_3$ | 240 |
| $C_6H_5Si(CH_3)_2$<br>$\quad\quad\;\;\|$<br>$\quad\quad CH_3NCOCH_3$ | 55 |
| $CF_3CH_2CH_2Si(CH_3)_2$<br>$\quad\quad\quad\quad\quad\;\;\|$<br>$\quad\quad\quad\quad\;\; CH_3NCOCH_3$ | 40 |
| 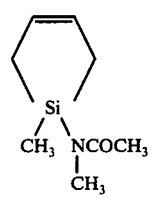 | less than 30 seconds |
| 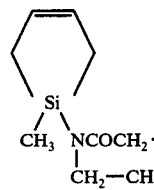 | less than 30 seconds |

EXAMPLE 4

When one mol of $CH_3\{(CH_3)_2SiO\}_4H$ is mixed with one mol of methylsilacyclopentenyl-N-methyl acetamide dissolved in an equal volume of anhydrous toluene, a good yield of

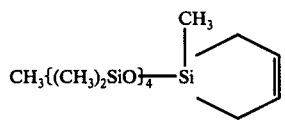

is obtained in less than one minute.

That which is claimed is:

1. A composition having the formula

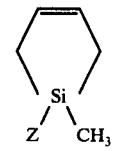

wherein Z is a monovalent amido radical.

2. A composition according to claim 1 wherein Z is N-methylacetamido.

3. A method for silylating an active-hydrogen-containing compound which comprises mixing a compound comprising at least one active hydrogen atom directly bonded to a heteroatom selected from the group consisting of oxygen, sulfur and nitrogen and a silylating agent having the formula

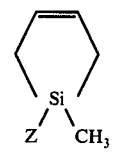

wherein Z is a monovalent amido radical whereby a compound comprising at least one radical of the formula

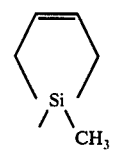

directly bonded to said heteroatom is obtained.

4. A method according to claim 3 wherein the active-hydrogen-containing compound is a carbon-containing compound.

5. A method according to claim 3 wherein the active-hydrogen-containing compound is a silicon-containing compound and the heteroatom bearing the active hydrogen atom is also bonded directly to a silicon atom of the silicon-containing compound.

6. A method according to claim 3 wherein the silylating agent is methylsilacyclopentenyl-N-methylacetamide.

* * * * *

UNITED STATES PATENT AND TRADEMARK OFFICE
CERTIFICATE OF CORRECTION

PATENT NO. : 4,104,295

DATED : August 1, 1978

INVENTOR(S) : Jerome M. Klosowski; Charles A. Romig

It is certified that error appears in the above-identified patent and that said Letters Patent are hereby corrected as shown below:

In Column 6, line 39; "C/C" should read "C≡C".

Signed and Sealed this

Twenty-second Day of September 1981

[SEAL]

Attest:

GERALD J. MOSSINGHOFF

Attesting Officer

Commissioner of Patents and Trademarks